(12) United States Patent
Nakatani

(10) Patent No.: US 7,534,892 B2
(45) Date of Patent: May 19, 2009

(54) SULFONAMIDE COMPOUND

(75) Inventor: Takuji Nakatani, Osaka (JP)

(73) Assignee: Shionogi & Co., Ltd., Osaka-Shi, Osaka (JP)

( * ) Notice: Subject to any disclaimer, the term of this patent is extended or adjusted under 35 U.S.C. 154(b) by 0 days.

(21) Appl. No.: 11/630,196

(22) PCT Filed: Jun. 23, 2005

(86) PCT No.: PCT/JP2005/011492

§ 371 (c)(1),
(2), (4) Date: Dec. 21, 2006

(87) PCT Pub. No.: WO2006/001318

PCT Pub. Date: Jan. 5, 2006

(65) Prior Publication Data

US 2007/0287710 A1    Dec. 13, 2007

(30) Foreign Application Priority Data

Jun. 24, 2004  (JP) .............................. 2004-185922

(51) Int. Cl.
*C07D 401/12* (2006.01)
*C07D 211/56* (2006.01)
(52) U.S. Cl. ...................... 546/207; 546/223
(58) Field of Classification Search ............ 546/207, 546/223
See application file for complete search history.

(56) References Cited

U.S. PATENT DOCUMENTS 6,699,891 B1 * 3/2004 Kawanishi et al. .......... 514/352

FOREIGN PATENT DOCUMENTS

| EP | 1 249 233 A1 | 10/2002 |
| EP | 1 484 301 A1 | 12/2004 |
| WO | WO-01/37826 A1 | 5/2001 |
| WO | WO-03/076374 A1 | 9/2003 |
| WO | WO-2005/103050 | 11/2005 |

OTHER PUBLICATIONS

Vippagunta, et al. Advanced Drug Delivery Reviews. 48 (2001) 3-26.*
Database CA [Online] Chemical Abstracts Service, Columbus, Ohio, US; Barboiu, Mihai et al., "Carbonic anhydrase inhibitors. Part 75. Synthesis of topically effective intraocular pressure lowering agents derived from 5-(.omega.-amino-alkylcarboxamido)-1,3,4-thiadiazol-2-sulfonamide" J. Enzyme Inhibition, vol. 15, pp. 23-46, 1999 XP002476253, retrieved from STN Database accession No. 2000:368338.
Database CA [Online] Chemical Abstracts service, Columbus, Ohio, US; Horstmann, H. et al., "Sulfonamides with schistosomal activity", XP002476254, retrieved from STN Database accession No. 1978-540207 abstract.
Grundemar et al., Trends in Pharmacological Sciences, vol. 15, pp. 153-159, May 1994.
Betancur et al., Trends in Pharmacological Sciences, vol. 18, pp. 372-386, Oct. 1997.
Balasubramaniam, Peptides, vol. 18, No. 3, pp. 445-457, 1997.

* cited by examiner

*Primary Examiner*—Rebecca L Anderson
*Assistant Examiner*—Shawquia Young
(74) *Attorney, Agent, or Firm*—Birch, Stewart, Kolasch & Birch, LLP

(57) ABSTRACT

The present invention provides a compound of the formula (I):

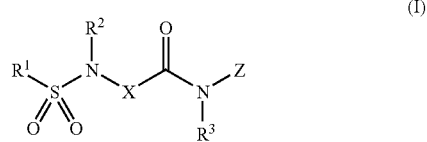

(wherein, $R^1$ is ethyl optionally substituted by halogen or amino optionally substituted by lower alkyl,
$R^2$ and $R^3$ are each independently hydrogen or lower alkyl,
X is cycloalkylene, lower alkylene or piperidinediyl,
Z is optionally substituted phenyl or optionally substituted heterocyclyl) prodrug, pharmaceutically acceptable salt or solvate thereof.

5 Claims, No Drawings

SULFONAMIDE COMPOUND

FIELD OF THE INVENTION

This invention relates to a new compound having NPYY5 receptor antagonist activity or a pharmaceutical composition comprising thereof. In more detail, it relates to an anti-obestic agent or anorectic agent.

PRIOR ART

Neuropeptide Y (hereinafter referred to as NPY) is a peptide which consists of 36 amino acid residues and was isolated from porcine brain in 1982. NPY is widely distributed in the central nervous system and peripheral tissues of humans and animals.

It has been reported that NPY possesses a stimulating activity of food intake, an anti-seizure activity, a learning-promoting activity, an anti-anxiety activity, an anti-stress activity etc. in central nervous system, and it may be pivotally involved in the central nervous system diseases such as depression, Alzheimer's disease and Parkinson's disease. NPY is thought to be associated with the cardiovascular diseases, since it induces a contraction of smooth muscles such as blood vessels or cardiac muscles in the peripheral tissues. Furthermore, NPY is also known to be involved in the metabolic diseases such as obesity, diabetes, and hormone abnormalities (Non-patent Document 1). Therefore, an NPY receptor antagonist is expected as a medicine for preventing or treating various diseases involved in the NPY receptor like the above.

Subtypes of Y1, Y2, Y3, Y4, Y5, and Y6 have now been identified as the NPY receptor (Non-patent Document 2). It has been suggested that the Y5 receptor is at least involved in the feeding behavior and its antagonist is expected as an anti-obestic agent (Non-patent Document 3).

Compounds having similar structures to those of the compounds of the present invention and having NPY receptor antagonist activity are described in Patent Document 1. However, an ethyl sulfonamide compound or an amino sulfonamide compound whose amino is substituted by alkyl is not disclosed in particular in the document.

Non-patent Document 1: Trends in Pharmacological Sciences, Vol. 15, pp. 153 (1994)
Non-patent Document 2: Trends in Pharmacological Sciences, Vol. 18, pp. 372 (1997)
Non-patent Document 3: Peptides, Vol. 18, pp. 445 (1997)
Patent Document 1: WO01/37826

DISCLOSURE OF INVENTION

Problems to be Solved by the Invention

The object of the present invention is to provide a new compound having superior NPYY5 receptor antagonist activity and a pharmaceutical composition comprising thereof.

Means to Solve the Problems
This invention provides
1) a compound of the formula (I):

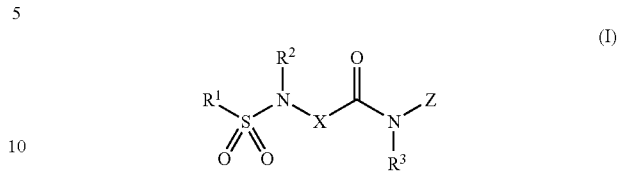

(wherein, $R^1$ is ethyl optionally substituted by halogen or amino optionally substituted by lower alkyl,
$R^2$ and $R^3$ are each independently hydrogen or lower alkyl,
X is cycloalkylene, lower alkylene or piperidinediyl,
Z is optionally substituted phenyl or optionally substituted heterocyclyl), pharmaceutically acceptable salt or solvate thereof,
2) the compound described in the above 1) wherein X is C2-C4 alkylene,

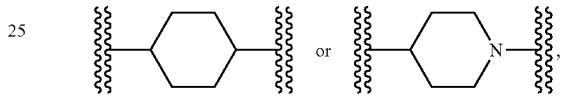

pharmaceutically acceptable salt or solvate thereof,
3) the compound described in 1) or 2) wherein Z is
(i) phenyl optionally substituted by one or more substituent(s) selected from morpholino substituted by lower alkyl, halogeno lower alkyl, lower alkoxy, lower alkoxycarbonyl, lower alkylene dioxy or halogeno lower alkylene dioxy,
(ii) pyridyl optionally substituted by one or more substituent(s) selected from halogeno lower alkyl or halogeno lower alkoxy,
(iii) carbazolyl optionally substituted by lower alkyl or tetrahydrocarbazolyl optionally substituted by lower alkyl,
(iv) benzofuryl optionally substituted by one or more substituent(s) selected from lower alkoxy, lower alkoxycarbonyl or lower alkyl carbamoyl,
(v) chromenyl optionally substituted by oxo or
(vi) cycloheptabenzofuryl, pharmaceutically acceptable salt or solvate thereof,
4) the compound described in any one of the above 1) to 3) wherein both $R^2$ and $R^3$ are hydrogen, pharmaceutically acceptable salt or solvate thereof,
5) a pharmaceutical composition comprising the compound described in any one of 1) to 4), pharmaceutically acceptable salt or solvate thereof,
6) a NPYY5 receptor antagonist comprising the compound described in any one of 1) to 4), pharmaceutically acceptable salt or solvate thereof Effect Of The Invention
A compound of this invention has NPYY5 receptor antagonist activity. Therefore, a compound of this invention can be very useful as an anti-obestic agent or anorectic agent.

BEST MODE FOR CARRYING OUT THE INVENTION

In this description, "halogen" includes fluorine, chlorine, bromine and iodine. Fluorine is especially preferable. The halogen part in "halogeno lower alkyl", "halogeno lower alkylenedioxy", "halogeno lower alkoxy", "halogeno lower alkoxycarbonyl" or "halogeno lower alkyl carbamoyl" is the same as above.

The term "lower alkyl" includes C1 to C10 straight or branched alkyl. The examples of "lower alkyl" are methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl and n-nonyl, n-decyl.

The lower alkyl part in "morpholino substituted by lower alkyl", "halogeno lower alkyl", "lower alkoxy", "halogeno lower alkoxy", "lower alkoxycarbonyl", "halogeno lower alkoxycarbonyl", "lower alkylcarbamoyl", "halogeno lower alkylcarbamoyl", "heterocyclyl substituted by lower alkyl" or "lower alkylcarbonyl" is the same as above.

"Lower alkyl" in $R^2$ and $R^3$ or lower alkyl in "amino optionally substituted by lower alkyl" of $R^1$ is preferably C1 to C3 alkyl and more preferably methyl.

The term "cycloalkyl" includes C3 to C8 cyclic alkyl and preferably C5 or C6 cyclic alkyl. Examples are cyclopropyl, cyclobutyl, cyclopentyl, cyclohexyl, cycloheptyl and cyclooctyl.

The cycloalkyl part in "cycloalkylcarbonyl" is the same as above.

The term "cycloalkylene" includes C3 to C8 cyclic alkylene and preferably C5 or C6 cyclic alkylene. Examples are cyclopropylene, cyclobutylene, cyclopentylene, cyclohexylene, cycloheptylene and cyclooctylene, preferably cyclohexylene and especially preferably 1,4-cyclohexanediyl.

The term "lower alkylene" includes a bivalent group comprising 1 to 6 of methylene, preferably 2 to 6 of methylene and more preferably 3 to 6 of methylene. Examples are methylene, ethylene, trimethylene, tetramethylene, pentamethylene and hexamethylene and especially preferably tetramethylene.

The lower alkylene part in "lower alkylenedioxy" and "halogeno lower alkylenedioxy" is the same as above and preferably methylenedioxy or ethylenedioxy.

The term "lower alkenyl" includes C2 to C10, preferably C2 to C8 and more preferably C3 to C6 straight or branched alkenyl having one or more double bonds at any possible positions. Examples are vinyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl and decenyl.

The lower alkenyl part in "lower alkenylcarbonyl" is the same as above.

The term "aryl carbonyl" includes benzoylcarbonyl and naphthylcarbonyl.

The examples of a substituent in "optionally substituted phenyl" are halogen, hydroxy, lower alkyl, halogeno lower alkyl, lower alkoxy, halogeno lower alkoxy, carboxy, lower alkoxycarbonyl, halogeno lower alkoxycarbonyl, acyl, acyloxy, carbamoyl, lower alkyl carbamoyl, halogeno lower alkyl carbamoyl, phenyl optionally substituted by a substituents group a, heterocyclyl optionally substituted by a substituents group a(wherein a substituents group a is halogen, hydroxy, lower alkyl, halogeno lower alkyl, lower alkoxy, halogeno lower alkoxy or the like), lower alkylenedioxy, halogeno lower alkylenedioxy, oxo and the like. The substituent can be substituted by one or more substituent(s) selected from the above substituents.

Preferred is heterocyclyl substituted by lower alkyl, lower alkyl, halogeno lower alkyl, lower alkoxy, halogeno lower alkoxy, carboxy, lower alkoxycarbonyl, halogeno lower alkoxycarbonyl, lower alkylenedioxy or halogeno lower alkylenedioxy.

The term "heterocyclyl" includes heterocyclyl containing one or more heteroatom arbitrarily selected from O, S and N in the ring. For example, 5- or 6-membered heteroaryl such as pyrrolyl, imidazolyl, pyrazolyl, pyridyl, pyridazinyl, pyrimidinyl, pyrazinyl, triazolyl, triazinyl, tetrazolyl, isoxazolyl, oxazolyl, oxadiazolyl, isothiazolyl, thiazolyl, thiadiazolyl, furyl and thienyl; non-aromatic heterocyclyl such as dioxanyl, thiiranyl, oxiranyl, oxathiolanyl, azetidinyl, thianyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, tetrahydrofuryl, tetrahydropyranyl, tetrahydrothiazolyl and tetrahydroisothiazolyl; fused heterocyclyl consisting of two rings such as indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, chromenyl, benzimidazolyl, benzisoxazolyl, benzoxazolyl, benbzoxadiazolyl, benzisothiazolyl, benzothiazolyl, benzothiadiazolyl, benzofuryl, isobenzofuryl, benzothienyl, benzotriazolyl, imidazopyridyl, triazoropyridyl, imidazothiazolyl, pyrazinopyridazinyl, quinazolinyl, quinolyl, isoquinolyl, naphthyridinyl, dihydropyridyl, tetrahydroquinolyl and tetrahydrobenzothienyl; and fused heterocyclyl consisting of three rings such as carbazolyl, tetrahydrocarbazolyl, acridinyl, xanthenyl, phenothiazinyl, phenoxathiinyl, phenoxazinyl, dibenzofuryl, cyclohexabenzofuryl and cycloheptabenzofuryl.

Preferred is pyridyl, carbazol, tetrahydrocarbazolyl, benzofuryl or cycloheptabenzofuryl.

A fused heterocyclyl condensed with a ring except for heterocyclyl (e.g., benzofuryl) can have bonds on any of the rings.

The heterocyclyl part in "heterocyclyl substituted by lower alkyl" is the same as above and preferably is morpholinyl.

Substituents for "optionally substituted heterocyclyl" are the same as those for the above "optionally substituted phenyl", which are optionally substituted with one or more substituents selected from them. Preferred is lower alkyl, halogeno lower alkyl, halogeno lower alkoxy, lower alkoxy, lower alkoxycarbonyl and lower alkyl carbamoyl, oxo or the like.

The heterocyclyl part in "heterocyclyl optionally substituted by a substituents group a" is preferably morpholino, morpholyl, thiomorpholino, thio morpholinyl or the like.

The term "acyl" includes (1) C1 to C10, preferably C1 to C6 and more preferably C1 to C4 straight or branched lower alkylcarbonyl or C2 to C10, preferably C2 to C8 and more preferably C3 to C6 straight or branched lower alkenylcarbonyl, (2) C4 to C9 and preferably C4 to C7 cycloalkylcarbonyl and (3) arylcarbonyl. Examples are formyl, acetyl, propionyl, butyryl, isobutyryl, valeryl, pivaloyl, hexanoyl, acryloyl, propioloyl, methacryloyl, crotonoyl, cyclopropylcarbonyl, cyclohexylcarbonyl, cyclooctylcarbonyl and benzoyl.

The "acyl" part in "acyloxy" is the same as above.

The compounds of the present invention include any formable and pharmaceutically acceptable salts thereof. Examples of "the pharmaceutically acceptable salt" are salts with mineral acids such as hydrochloric acid, sulfuric acid, nitric acid and phosphoric acid; salts with organic acids such as para-toluenesulfonic acid, methanesulfonic acid, oxalic acid and citric acid; salts with organic bases such as ammonium, trimethylammonium and triethylammonium; salts with alkaline metals such as sodium and potassium; and salts with alkaline earth metals such as calcium and magnesium.

The compounds of the present invention include solvates thereof. Hydrate is preferable and arbitrary numbers of solvent molecules may coordinate to the compound (I).

When the compound (I) of the present invention has an asymmetric carbon atom, it includes racemates, all of enantiomers and all of stereoisomers such as diastereomer, epimer and enantiomer thereof. Additionally, when the compound (I) of the present invention having a double bond forms an E isomer or Z isomer, the compound (I) includes both isomers. When X is cycloalkylene, the compound (I) includes both of cis isomer and trans isomer.

For example, the compound (I) of the present invention can be synthesized by the methods described in Patent Document 1 or the following methods.

[Chemical structures showing Compound (IV) + Compound (V) → Step A → Compound (II) + Compound (III) → Step B → Compound (I)]

(wherein Hal is halogen and the other symbols are the same as above.)

Step A

Compound (IV) is reacted with Compound (V) having substituent $R^1$ corresponding to a target compound in a suitable solvent, if necessary, under the presence of the base to give Compound (II).

Examples of the solvent are tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile, water and mixture thereof. Preferred is dioxane, dichloromethane or the like.

Examples of the base are sodium hydroxide, potassium hydroxide, lithium hydroxide or the like.

The reaction temperature is about 0° C. to 50° C. and preferably about 20° C. to 30° C.

The reaction time is about 5 minutes to 30 hours and preferably about 5 to 20 hours.

As Compound (IV) and (V), a well-known compound or a compound synthesized by well-known method from a well-known compound can be used.

Step B

Compound (II) and Compound (III) having substituent Z and $R^3$ corresponding to a target compound are reacted in an appreciate solvent.

Examples of solvents are tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile, water and mixture thereof. Preferred is dimethylformamide, tetrahydrofuran, ethyl acetate or the like.

If necessary, the reaction can be carried under the presence of a condensing agent such as 1,3-dicyclohexylcarbodiimide, 1-ethyl 3-(3-dimethylamino) carbodiimide (WSCD; water-soluble carbodiimide) and an acidic excipient such as 1-hydroxy benzotriazole, 3,4-dihydro-3-hydroxy-4-oxo 1,2,3-benzotriazine.

The reaction temperature is about 0° C. to 50° C. and preferably about 20° C. to 30° C.

The reaction time is about 5 minutes to 30 hours and preferably about 5 to 20 hours.

Amino groups may be protected with a suitable protecting group in the usual manner at a suitable step. For example, phthalimide, lower alkoxycarbonyl, lower alkenyloxycarbonyl, halogenoalkoxycarbonyl, aryl lower alkoxycarbonyl, trialkylsilyl, lower alkylsulfonyl, halogeno lower alkylsulfonyl, arylsulfonyl, lower alkylcarbonyl and arylcarbonyl can be used as the protecting group.

After protection, the compound is subjected to the above-mentioned reactions and the obtained compound is deprotected by treatment of an acid or a base in a suitable solvent at a suitable stage. Examples of solvents are tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile and mixture thereof. Examples of a base are hydrazine, pyridine, sodium hydroxide and potassium hydroxide and examples of an acid are hydrochloric acid, trifluoroacetic acid and hydrofluoric acid.

All compounds of the present invention have NPYY5 receptor antagonist activity and the antagonist activity can be confirmed with the following test method.

cDNA sequence encoding a human NPY Y5 receptor (WO96/16542) is cloned in the expression vector pME18S (Takebe et al. Mol. Cell. Biol. 8, 8957). The obtained expression vector is transfected into a host CHO cells by using a Lipofect AMINE reagent (Trademark, Gibco BRL Co., Ltd.) according to an instruction protocol to obtain the cells that stably express NPY Y5 receptor.

The membranes prepare from the CHO cells expressing NPY Y5 receptor, the compound of the present invention and 50,000-70,000 cpm [$^{125}$I] peptide YY (100-140 pM of final concentration: Amersham) are incubated in the assay buffer (20 mM HEPES-Hanks buffer containing 0.1% bovine serum albumin, pH 7.4) at 25° C. for 2 hours, and then the mixture is filtered with a glass filter GF/B (treated with 0.5% polyethyleneimine and 0.25% bovine serum albumin). After the glass filter is washed with assay buffer, the radioactivity on the glass filter is measured with a gamma counter. The 50% inhibitory concentration of a compound of this invention against the specific peptide YY binding ($IC_{50}$ value) is calculated. The 50% inhibitory concentration of a compound of this invention against the unspecific binding is calculated by measuring the radioactivity on the glass filter after membrane preparation is incubated under the presence of 1 μM NPYY5 agonist ([cPP$^{1-7}$, NPY$^{19-23}$, Ala$^{31}$,Aib$^{32}$,Gln$^{34}$]-hPancreatic Polypeptide: Tocris Coockson) and 50,000-70,000 cpm of [$^{125}$I] peptide YY.

In all of the compounds of the present invention, the following compounds are especially preferable.

In the formula (I), (A1) a compound wherein $R^1$ is unsubstituted ethyl (hereinafter referred to as "$R^1$ is A1), (A2) a compound wherein $R^1$ is trifluoroethyl (hereinafter referred to as "$R^1$ is A2"), (A3) a compound wherein $R^1$ is dimethylamino (hereinafter referred to as "$R^1$ is A3"), (B1) a compound wherein $R^2$ and $R^3$ are each independently hydrogen or methyl (hereinafter referred to as "$R^2$ and $R^3$ are B1"), (B2) a compound wherein R² and R³ are both hydrogen (hereinafter referred to as "R² and R³ are B2"),
(C1) a compound wherein X is cyclohexylene (hereinafter referred to as "X is C1"),
(C2) a compound wherein X is dimethylene (hereinafter referred to as "X is C2"),
(C3) a compound wherein X is tetramethylene (hereinafter referred to as "X is C3"),
(C4) a compound wherein X is piperidinediyl (hereinafter referred to as "X is C4"),
(D1a) a compound wherein Z is phenyl optionally substituted by one or more substituent(s) selected from morpholino substituted by lower alkyl, halogeno lower alkyl, lower alkoxy, lower alkoxycarbonyl, lower alkylenedioxy or halogeno lower alkylenedioxy (hereinafter referred to as "Z is D1a"),
(D1b) a compound wherein Z is phenyl optionally substituted by one or more substituent(s) selected from dimethylmorpholino, trifluoromethyl, methoxy, methoxycarbonyl, methylenedioxy, difluoromethylenedioxy or tetrafluoroethylenedioxy (hereinafter referred to as Z is "D1b"),
(D2a) a compound wherein Z is pyridyl optionally substituted by one or more substituent(s) selected from halogeno lower alkyl or halogeno lower alkoxy (hereinafter referred to as "Z is D2a"),
(D2b) a compound wherein Z is pyridyl optionally substituted trifluoromethyl or trifluoroethoxy (hereinafter referred to as "Z is D2b"),
(D3a) a compound wherein Z is carbazolyl optionally substituted by lower alkyl or tetrahydrocarbazolyl optionally substituted by lower alkyl (hereinafter referred to as "Z is D3a"),
(D3b) a compound wherein Z is carbazolyl optionally substituted by ethyl or isopropyl or tetrahydrocarbazolyl optionally substituted by ethyl or isopropyl (hereinafter referred to as "Z is D3b"),
(D4a) a compound wherein Z is benzofuryl optionally substituted by one or more substituent(s) selected from lower alkoxy, lower alkoxycarbonyl or lower alkyl carbamoyl (hereinafter referred to as "Z is D4a"),
(D4b) a compound wherein Z is benzofuryl optionally substituted by one or more substituent(s) selected from methoxy, methoxycarbonyl or isopropylcarbamoyl (hereinafter referred to as "Z is D4b"),
(D5) a compound wherein Z is chromenyl optionally substituted by oxo (hereinafter referred to as "Z is D5"),
(D6) a compound wherein Z is cycloheptabenzofuryl (hereinafter referred to as "Z is D6"),
(E) a compound wherein a combination of R¹, R² and R³, X and Z (R¹, R² and R³, X, Z) is any one of the followings, (R¹, R² and R³, X, Z)=(A1, B1, C1, D1a), (A1, B1, C1, D1b), (A1, B1, C1, D2a), (A1, B1, C1, D2b), (A1, B1, C1, D3a), (A1, B1, C1, D3b), (A1, B1, C1, D4a), (A1, B1, C1, D4b), (A1, B1, C1, D5), (A1, B1, C1, D6), (A1, B1, C2, D1a), (A1, B1, C2, D1b), (A1, B1, C2, D2a), (A1, B1, C2, D2b), (A1, B1, C2, D3a), (A1, B1, C2, D3b), (A1, B1, C2, D4a), (A1, B1, C2, D4b), (A1, B1, C2, D5), (A1, B1, C2, D6), (A1, B1, C3, D1a), (A1, B1, C3, D1b), (A1, B1, C3, D2a), (A1, B1, C3, D2b), (A1, B1, C3, D3a), (A1, B1, C3, D3b), (A1, B1, C3, D4a), (A1, B1, C3, D4b), (A1, B1, C3, D5), (A1, B1, C3, D6), (A1, B1, C4, D1a), (A1, B1, C4, D1b), (A1, B1, C4, D2a), (A1, B1, C4, D2b), (A1, B1, C4, D3a), (A1, B1, C4, D3b), (A1, B1, C4, D4a), (A1, B1, C4, D4b), (A1, B1, C4, D5), (A1, B1, C4, D6), (A1, B2, C1, D1a), (A1, B2, C1, D1b), (A1, B2, C1, D2a), (A1, B2, C1, D2b), (A1, B2, C1, D3a), (A1, B2, C1, D3b), (A1, B2, C1, D4a), (A1, B2, C1, D4b), (A1, B2, C1, D5), (A1, B2, C1, D6), (A1, B2, C2, D1a), (A1, B2, C2, D1b), (A1, B2, C2, D2a), (A1, B2, C2, D2b), (A1, B2, C2, D3a), (A1, B2, C2, D3b), (A1, B2, C2, D4a), (A1, B2, C2, D4b), (A1, B2, C2, D5), (A1, B2, C2, D6), (A1, B2, C3, D1a), (A1, B2, C3, D1b), (A1, B2, C3, D2a), (A1, B2, C3, D2b), (A1, B2, C3, D3a), (A1, B2, C3, D3b), (A1, B2, C3, D4a), (A1, B2, C3, D4b), (A1, B2, C3, D5), (A1, B2, C3, D6), (A1, B2, C4, D1a), (A1, B2, C4, D1b), (A1, B2, C4, D2a), (A1, B2, C4, D2b), (A1, B2, C4, D3a), (A1, B2, C4, D3b), (A1, B2, C4, D4a), (A1, B2, C4, D4b), (A1, B2, C4, D5), (A1, B2, C4, D6), (A2, B1, C1, D1a), (A2, B1, C1, D1b), (A2, B1, C1, D2a), (A2, B1, C1, D2b), (A2, B1, C1, D3a), (A2, B1, C1, D3b), (A2, B1, C1, D4a), (A2, B1, C1, D4b), (A2, B1, C1, D5), (A2, B1, C1, D6), (A2, B1, C2, D1a), (A2, B1, C2, D1b), (A2, B1, C2, D2a), (A2, B1, C2, D2b), (A2, B1, C2, D3a), (A2, B1, C2, D3b), (A2, B1, C2, D4a), (A2, B1, C2, D4b), (A2, B1, C2, D5), (A2, B1, C2, D6), (A2, B1, C3, D1a), (A2, B1, C3, D1b), (A2, B1, C3, D2a), (A2, B1, C3, D2b), (A2, B1, C3, D3a), (A2, B1, C3, D3b), (A2, B1, C3, D4a), (A2, B1, C3, D4b), (A2, B1, C3, D5), (A2, B1, C3, D6), (A2, B1, C4, D1a), (A2, B1, C4, D1b), (A2, B1, C4, D2a), (A2, B1, C4, D2b), (A2, B1, C4, D3a), (A2, B1, C4, D3b), (A2, B1, C4, D4a), (A2, B1, C4, D4b), (A2, B1, C4, D5), (A2, B1, C4, D6), (A2, B2, C1, D1a), (A2, B2, C1, D1b), (A2, B2, C1, D2a), (A2, B2, C1, D2b), (A2, B2, C1, D3a), (A2, B2, C1, D3b), (A2, B2, C1, D4a), (A2, B2, C1, D4b), (A2, B2, C1, D5), (A2, B2, C1, D6), (A2, B2, C2, D1a), (A2, B2, C2, D1b), (A2, B2, C2, D2a), (A2, B2, C2, D2b), (A2, B2, C2, D3a), (A2, B2, C2, D3b), (A2, B2, C2, D4a), (A2, B2, C2, D4b), (A2, B2, C2, D5), (A2, B2, C2, D6), (A2, B2, C3, D1a), (A2, B2, C3, D1b), (A2, B2, C3, D2a), (A2, B2, C3, D2b), (A2, B2, C3, D3a), (A2, B2, C3, D3b), (A2, B2, C3, D4a), (A2, B2, C3, D4b), (A2, B2, C3, D5), (A2, B2, C3, D6), (A2, B2, C4, D1a), (A2, B2, C4, D1b), (A2, B2, C4, D2a), (A2, B2, C4, D2b), (A2, B2, C4, D3a), (A2, B2, C4, D3b), (A2, B2, C4, D4a), (A2, B2, C4, D4b), (A2, B2, C4, D5), (A2, B2, C4, D6), (A3, B1, C1, D1a), (A3, B1, C1, D1b), (A3, B1, C1, D2a), (A3, B1, C1, D2b), (A3, B1, C1, D3a), (A3, B1, C1, D3b), (A3, B1, C1, D4a), (A3, B1, C1, D4b), (A3, B1, C1, D5), (A3, B1, C1, D6), (A3, B1, C2, D1a), (A3, B1, C2, D1b), (A3, B1, C2, D2a), (A3, B1, C2, D2b), (A3, B1, C2, D3a), (A3, B1, C2, D3b), (A3, B1, C2, D4a), (A3, B1, C2, D4b), (A3, B1, C2, D5), (A3, B1, C2, D6), (A3, B1, C3, D1a), (A3, B1, C3, D1b), (A3, B1, C3, D2a), (A3, B1, C3, D2b), (A3, B1, C3, D3a), (A3, B1, C3, D3b), (A3, B1, C3, D4a), (A3, B1, C3, D4b), (A3, B1, C3, D5), (A3, B1, C3, D6), (A3, B1, C4, D1a), (A3, B1, C4, D1b), (A3, B1, C4, D2a), (A3, B1, C4, D2b), (A3, B1, C4, D3a), (A3, B1, C4, D3b), (A3, B1, C4, D4a), (A3, B1, C4, D4b), (A3, B1, C4, D5), (A3, B1, C4, D6), (A3, B2, C1, D1a), (A3, B2, C1, D1b), (A3, B2, C1, D2a), (A3, B2, C1, D2b), (A3, B2, C1, D3a), (A3, B2, C1, D3b), (A3, B2, C1, D4a), (A3, B2, C1, D4b), (A3, B2, C1, D5), (A3, B2, C1, D6), (A3, B2, C2, D1a), (A3, B2, C2, D1b), (A3, B2, C2, D2a), (A3, B2, C2, D2b), (A3, B2, C2, D3a), (A3, B2, C2, D3b), (A3, B2, C2, D4a), (A3, B2, C2, D4b), (A3, B2, C2, D5), (A3, B2, C2, D6), (A3, B2, C3, D1a), (A3, B2, C3, D1b), (A3, B2, C3, D2a), (A3, B2, C3, D2b), (A3, B2, C3, D3a), (A3, B2, C3, D3b), (A3, B2, C3, D4a), (A3, B2, C3, D4b), (A3, B2, C3, D5), (A3, B2, C3, D6), (A3, B2, C4, D1a), (A3, B2, C4, D1b), (A3, B2, C4, D2a), (A3, B2, C4, D2b), (A3, B2, C4, D3a), (A3, B2, C4, D3b), (A3, B2, C4, D4a), (A3, B2, C4, D4b), (A3, B2, C4, D5) or (A3, B2, C4, D6), the pharmaceutically acceptable salt or solvate thereof A compound of the present invention is effective for all of the diseases in which NPY Y5 is involved and it is especially useful for preventing and/or treating obesity and suppressing food intake. Moreover, a compound is effective for preventing and/or treating the diseases in which obesity acts as a risk factor, for example, diabetes, hypertension, hyperlipemia, atherosclerosis and acute coronary syndrome.

Furthermore, a compound of the present invention has the good characters, for example,
a) weak CYP enzyme inhibition
b) high water solubility
c) good drug disposition such as high bioavailability
d) low toxicity of anemia-inducing activity or the like
e) high metabolic stability
f) high Y5 receptor selectivity.

A compound of the present invention can be administered orally or parenterally as an anti-obestic agent or anorectic agent. In the case of oral administration, it may be in any usual form such as tablets, granules, powders, capsules, pills, solutions, syrups, buccal tablets and sublingual tablets. When the compound is parenterally administered, any usual form is preferable, for example, injections (e.g., intramuscular, intravenous), suppositories, endermic agents and vapors. Oral administration is particularly preferable because the compounds of the present invention show a high oral absorbability.

A pharmaceutical composition may be manufactured by mixing an effective amount of a compound of the present invention with various pharmaceutical additives suitable for the administration form, such as excipients, binders, moistening agents, disintegrators, lubricants and diluents. When the composition is of an injection, an active ingredient together with a suitable carrier can be sterilized to give a pharmaceutical composition.

Examples of the excipients include lactose, saccharose, glucose, starch, calcium carbonate and crystalline cellulose. Examples of the binders include methylcellulose, carboxymethylcellulose, hydroxypropylcellulose, gelatin and polyvinylpyrrolidone. Examples of the disintegrators include carboxymethylcellulose, sodium carboxymethylcellulose, starch, sodium alginate, agar and sodium lauryl sulfate. Examples of the lubricants include talc, magnesium stearate and macrogol. Cacao oil, macrogol, methylcellulose etc. may be used as base materials of suppositories. When the composition is manufactured as solutions, emulsified injections or suspended injections, dissolving accelerators, suspending agents, emulsifiers, stabilizers, preservatives, isotonic agents and the like may be added. For oral administration, sweetening agents, flavors and the like may be added.

Although the dosage of a compound of the present invention as an anti-obestic agent or anorectic agent should be determined in consideration of the patient's age and body weight, the type and degree of diseases, the administration route etc., a usual oral dosage for an adult is 0.05 to 100 mg/kg/day and preferable is 0.1 to 10 mg/kg/day. For parenteral administration, although the dosage highly varies with administration routes, a usual dosage is 0.005 to 10 mg/kg/day, preferably, 0.01 to 1 mg/kg/day. The dosage may be administered in one to several divisions per day.

The present invention is further explained by the following Examples, which are not intended to limit the scope of the present invention.

In the examples, the meaning of each abbreviation is as below.

| | |
|---|---|
| Me: | methyl |
| Et: | ethyl |
| iPr: | isopropyl |
| WSCD: | 1-ethyl 3-(3-dimethylamino) carbodiimide |

-continued

| | |
|---|---|
| DMF: | N,N-dimethylformamide |
| HOBt: | 1-hydroxybenzotriazole |

EXAMPLE

Example 1

(Step 1)

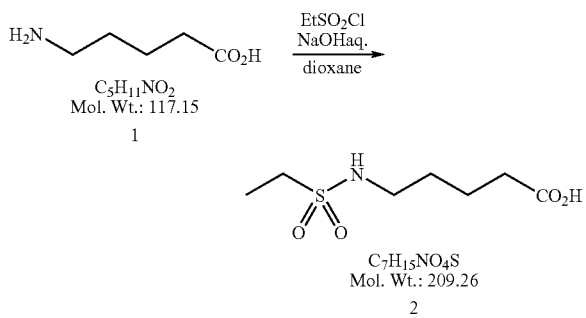

To suspension of 5-amino valeric acid 1 20.0 g (171 mmol) in dioxane 200 ml, was added 2 mol/L NaOH solution 200 ml (400 mmol) with stirring under ice. To this solution, was added ethane sulfonyl chloride 33.0 g (257 mmol) with stirring under ice for 10 minutes. The mixture was stirred at room temperature for 15 hours. The reaction solution was condensed to about half volume and water (200 ml) was added thereto. After adding 5 mol/L-HCl thereto to be acid, the mixture was extracted with ethyl acetate twice. The organic layer was washed with brine and dried over magnesium sulfate anhydrous. The solvent was evaporated under reduced pressure. Ether and hexane were added to the residue. The crystal deposited was filtrated to give 19.6 g of sulfonamide compound 2 (the yield is 55%).

$^1$H-NMR (CDCl$_3$); δ1.37 (3H, t, J=7.5 Hz), 1.67 (4H), 2.41 (2H, t, J=6.9 Hz), 3.05 (2H, q, J=7.5 Hz), 3.14 (2H, q, J=6.0 Hz), 4.81 (1H, t, J=6.0 Hz) ppm -continued

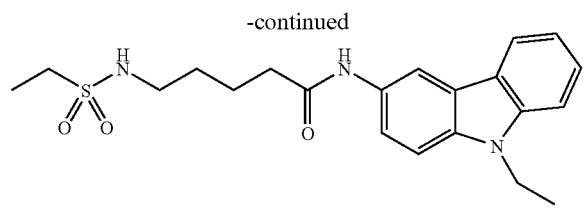

Id-2

To a solution of carboxylic acid 2 209 mg (1.00 mmol), 3-amino-N-ethyl carbazole 3 210 mg (1.00 mmol) and 1-hydroxybenzotriazole 163 mg (1.21 mmol) in N,N-dimethylformamide 5 ml, was added 1-ethyl 3-(3-dimethylamino) carbodiimide hydrochloride 231 mg (1.21 mmol). The mixture was stirred at room temperature for 15 hours. Water was added to the reaction solution and the crystal deposited was filtrated and washed with water and dried. The crude crystal obtained was purified with column chromatography ($SiO_2$ 10 g, $CHCl_3$/MeOH=50) and crystallized with diethyl ether to give 167 mg of the compound of this invention Id-2 (the yield is 42%).

Other Compounds (I) are synthesized by the same method as the above. The structures and physical properties are shown below.

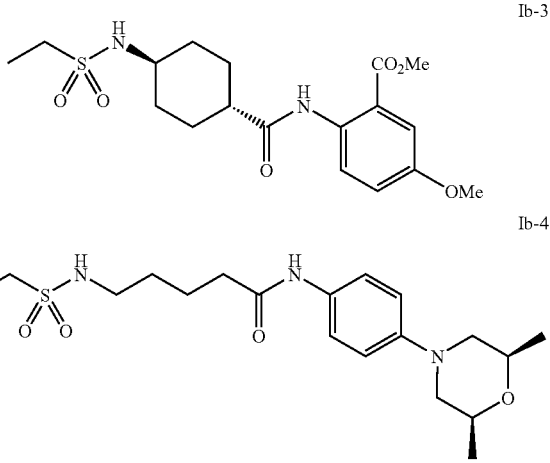

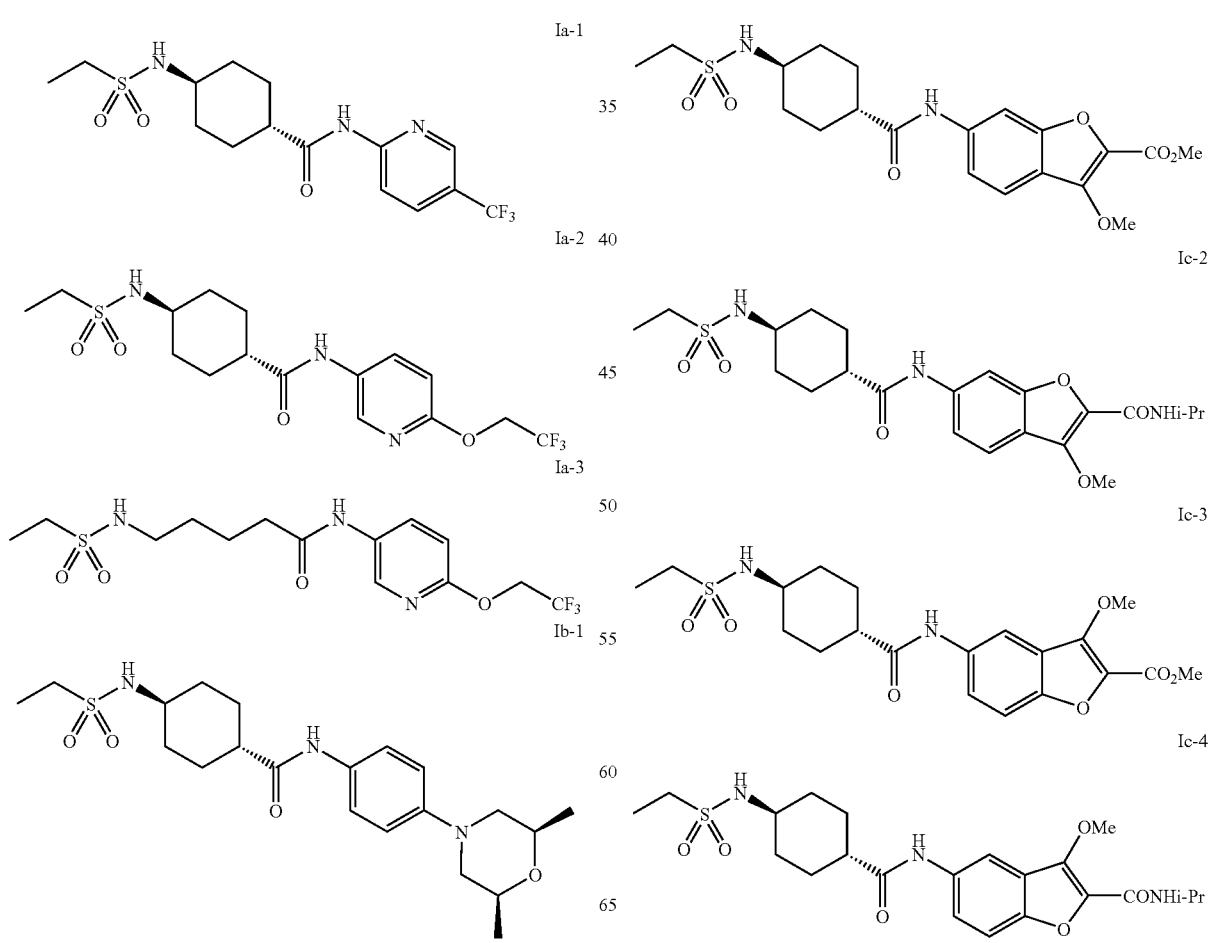

-continued
Id-1
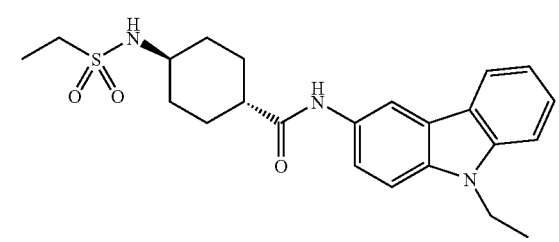
Id-2
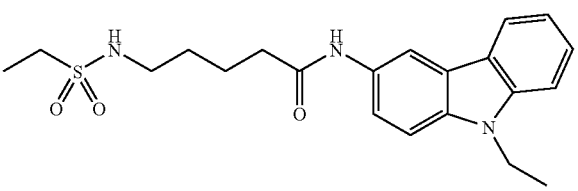
Id-3
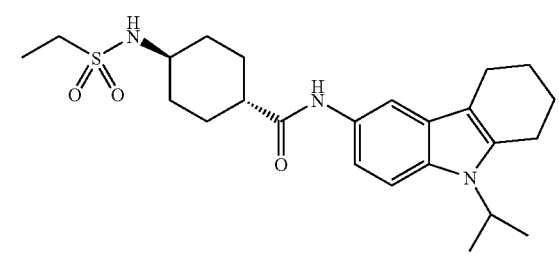
Id-4
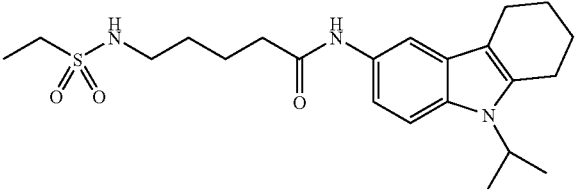
Ie-1
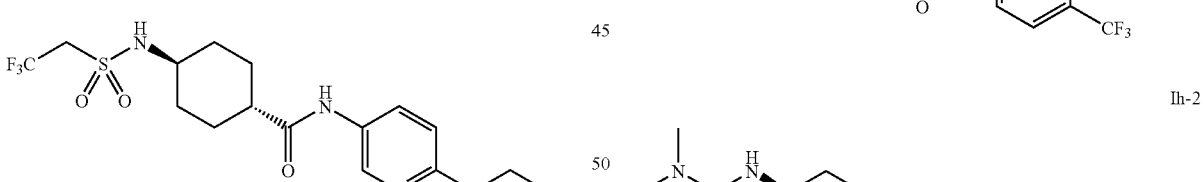
Ie-2
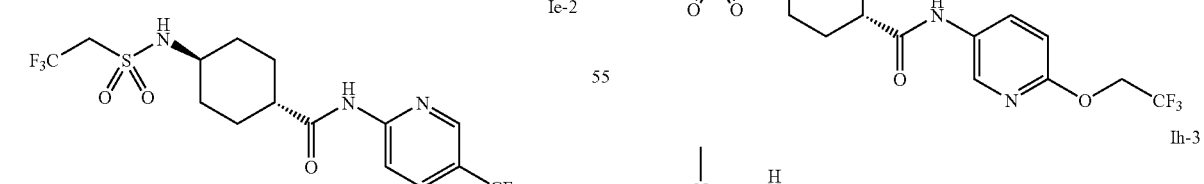
Ie-3
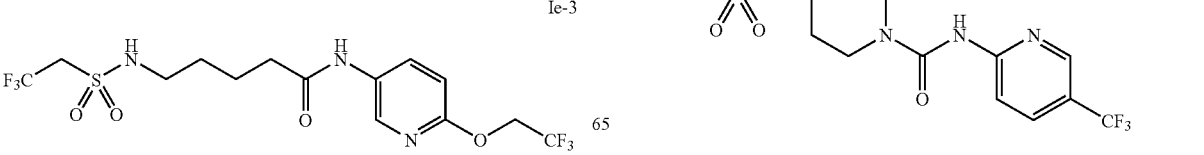
-continued
If-1
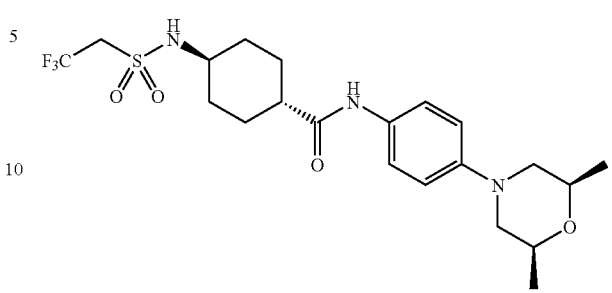
If-2
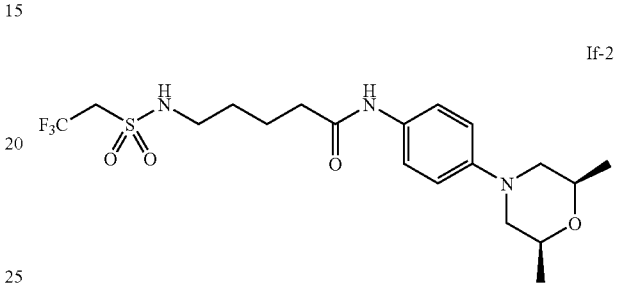
Ig-1
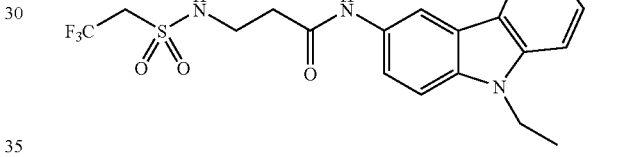
Ih-1
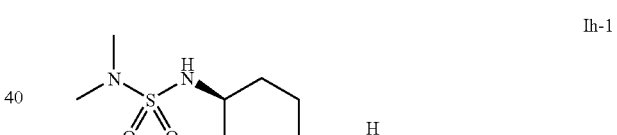
Ih-2
Ih-3
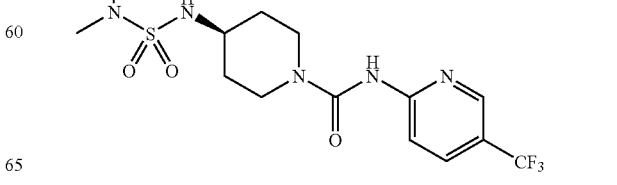

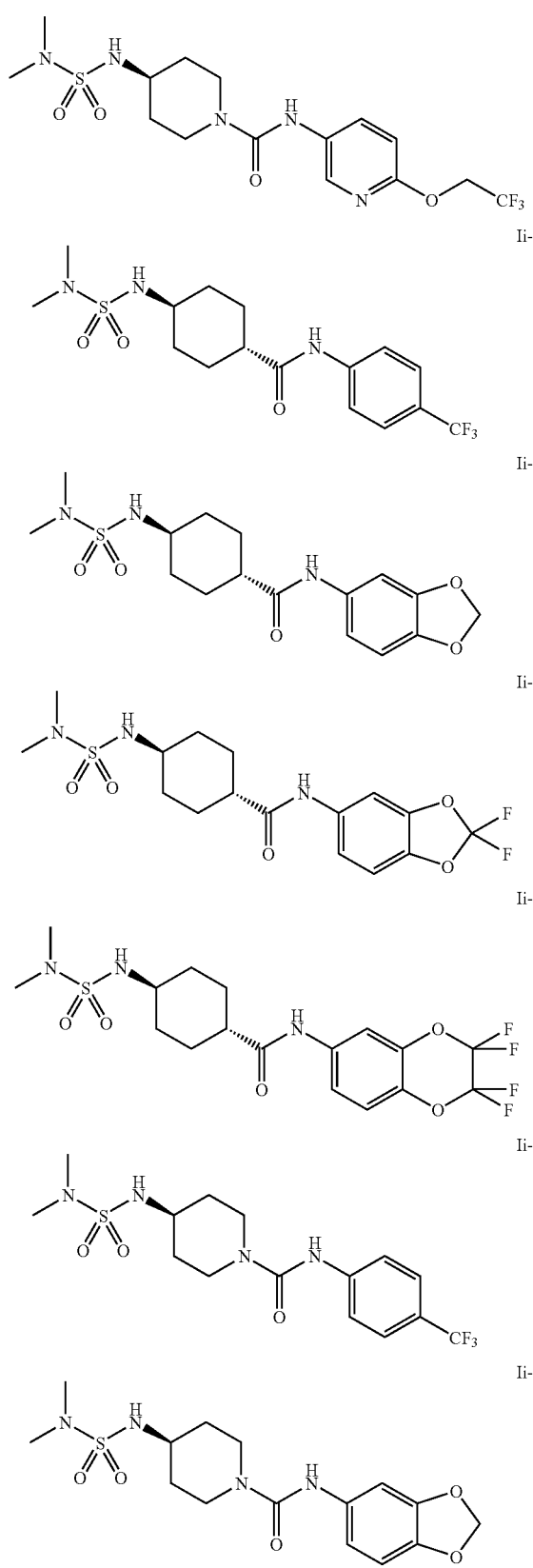

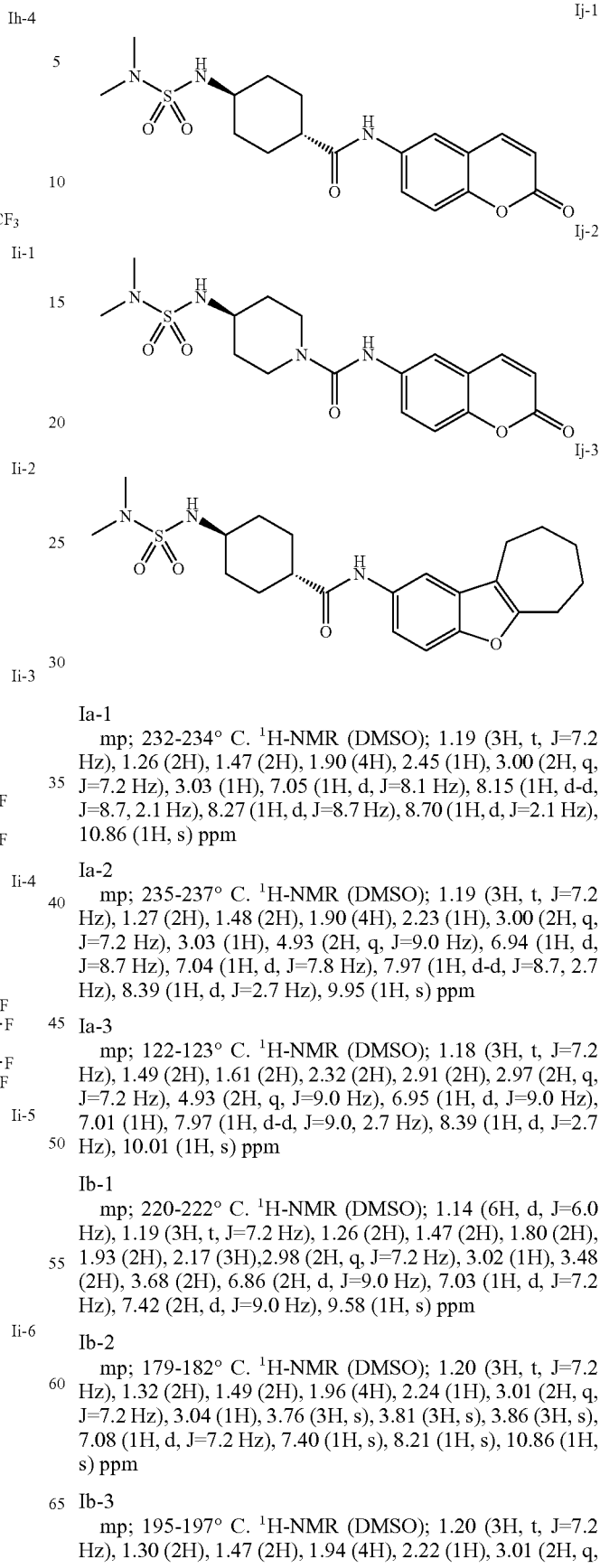

Ia-1
mp; 232–234° C. $^1$H-NMR (DMSO); 1.19 (3H, t, J=7.2 Hz), 1.26 (2H), 1.47 (2H), 1.90 (4H), 2.45 (1H), 3.00 (2H, q, J=7.2 Hz), 3.03 (1H), 7.05 (1H, d, J=8.1 Hz), 8.15 (1H, d-d, J=8.7, 2.1 Hz), 8.27 (1H, d, J=8.7 Hz), 8.70 (1H, d, J=2.1 Hz), 10.86 (1H, s) ppm Ia-2
mp; 235–237° C. $^1$H-NMR (DMSO); 1.19 (3H, t, J=7.2 Hz), 1.27 (2H), 1.48 (2H), 1.90 (4H), 2.23 (1H), 3.00 (2H, q, J=7.2 Hz), 3.03 (1H), 4.93 (2H, q, J=9.0 Hz), 6.94 (1H, d, J=8.7 Hz), 7.04 (1H, d, J=7.8 Hz), 7.97 (1H, d-d, J=8.7, 2.7 Hz), 8.39 (1H, d, J=2.7 Hz), 9.95 (1H, s) ppm Ia-3
mp; 122–123° C. $^1$H-NMR (DMSO); 1.18 (3H, t, J=7.2 Hz), 1.49 (2H), 1.61 (2H), 2.32 (2H), 2.91 (2H), 2.97 (2H, q, J=7.2 Hz), 4.93 (2H, q, J=9.0 Hz), 6.95 (1H, d, J=9.0 Hz), 7.01 (1H), 7.97 (1H, d-d, J=9.0, 2.7 Hz), 8.39 (1H, d, J=2.7 Hz), 10.01 (1H, s) ppm Ib-1
mp; 220–222° C. $^1$H-NMR (DMSO); 1.14 (6H, d, J=6.0 Hz), 1.19 (3H, t, J=7.2 Hz), 1.26 (2H), 1.47 (2H), 1.80 (2H), 1.93 (2H), 2.17 (3H), 2.98 (2H, q, J=7.2 Hz), 3.02 (1H), 3.48 (2H), 3.68 (2H), 6.86 (2H, d, J=9.0 Hz), 7.03 (1H, d, J=7.2 Hz), 7.42 (2H, d, J=9.0 Hz), 9.58 (1H, s) ppm Ib-2
mp; 179–182° C. $^1$H-NMR (DMSO); 1.20 (3H, t, J=7.2 Hz), 1.32 (2H), 1.49 (2H), 1.96 (4H), 2.24 (1H), 3.01 (2H, q, J=7.2 Hz), 3.04 (1H), 3.76 (3H, s), 3.81 (3H, s), 3.86 (3H, s), 7.08 (1H, d, J=7.2 Hz), 7.40 (1H, s), 8.21 (1H, s), 10.86 (1H, s) ppm Ib-3
mp; 195–197° C. $^1$H-NMR (DMSO); 1.20 (3H, t, J=7.2 Hz), 1.30 (2H), 1.47 (2H), 1.94 (4H), 2.22 (1H), 3.01 (2H, q, J=7.2 Hz), 3.04 (1H), 3.77 (3H, s), 3.83 (3H, s), 7.06 (1H, d, J=7.5 Hz), 7.19 (1H, d-d, J=9.0, 3.0 Hz), 7.35 (1H, d, J=3.0 Hz), 8.04 (1H, d, J=9.0 Hz), 10.26 (1H, s) ppm Ib-4 mp; 104-105° C. $^1$H-NMR (DMSO); 1.14 (6H, d, J=6.3 Hz), 1.17 (3H, t, J=7.2 Hz), 1.48 (2H), 1.59 (2H), 2.21 (4H), 2.93 (2H), 2.97 (2H, q, J=7.2 Hz), 3.48 (2H), 3.67 (2H), 6.86 (2H, d, J=9.0 Hz), 7.00 (1H), 7.42 (2H, d, J=9.0 Hz), 9.64 (1H, s) ppm Ic-1 mp; 262-264° C. $^1$H-NMR (DMSO); 1.20 (3H, t, J=7.2 Hz), 1.29 (2H), 1.50 (2H), 1.94 (4H), 2.29 (1H), 3.01 (2H, q, J=7.2 Hz), 3.05 (1H), 3.82 (3H, s), 4.21 (3H, s), 7.04 (1H, d, J=7.5 Hz), 7.39 (1H, d-d, J=8.7, 1.8 Hz), 7.90 (1H, d, J=8.7 Hz), 8.05 (1H, d, J=1.8 Hz), 10.19 (1H, s) ppm Ic-2 mp; 264-266° C. $^1$H-NMR (DMSO); 1.18 (6H, d, J=6.6 Hz), 1.20 (3H, t, J=7.5 Hz), 1.29 (2H), 1.51 (2H), 1.90 (4H), 2.28 (1H), 3.00 (2H, q, J=7.5 Hz), 3.04 (1H), 4.10 (1H), 4.16 (3H, s), 7.04 (1H, d, J=7.8 Hz), 7.37 (1H, d-d, J=8.7, 1.5 Hz), 7.64 (1H, d, J=8.1 Hz), 7.76 (1H, d, J=8.7 Hz), 8.07 (1H, d, J=1.5 Hz), 10.13 (1H, s) ppm Ic-3 mp; 235-237° C. $^1$H-NMR (DMSO); 1.20 (3H, t, J=7.2 Hz), 1.29 (2H), 1.49 (2H), 1.91 (4H), 2.26 (1H), 3.00 (2H, q, J=7.2 Hz), 3.04 (1H), 3.85 (3H, s), 4.16 (3H, s), 7.04 (1H, d, J=7.8 Hz), 7.57 (2H, br.-s), 8.33 (1H, br.-s), 10.00 (1H, s) ppm Ic-4 mp; 265-267° C. $^1$H-NMR (DMSO); 1.18 (6H, d, J=6.9 Hz), 1.20 (3H, t, J=7.5 Hz), 1.29 (2H), 1.51 (2H), 1.90 (4H), 2.26 (1H), 3.00 (2H, q, J=7.5 Hz), 3.04 (1H), 4.08 (1H), 4.12 (3H, s), 7.04 (1H, d, J=7.2 Hz), 7.05 (2H, br.-s), 7.82 (1H, d, J=8.1 Hz), 8.23 (1H, br.-s), 9.96 (1H, s) ppm Id-1 mp; 239-240° C. $^1$H-NMR (DMSO); 1.21 (3H, t, J=7.2 Hz), 1.29 (3H, t, J=7.2 Hz), 1.30 (2H), 1.54 (2H), 1.93 (4H), 2.28 (1H), 3.01 (2H, q, J=7.2 Hz), 3.05 (1H), 4.41 (2H, q, J=7.2 Hz), 7.05 (1H, d, J=7.5 Hz), 7.16 (1H, t, J=7.5 Hz), 7.43 (1H, t, J=7.5 Hz), 7.54 (3H), 8.04 (1H, d, J=7.8 Hz), 8.43 (1H, s), 9.82 (1H, s) ppm Id-2 mp; 117° C. $^1$H-NMR (DMSO); 1.19 (3H, t, J=7.2 Hz), 1.30 (3H, t, J=7.2 Hz), 1.54 (2H), 1.67 (2H), 2.35 (2H, t, J=7.2 Hz), 2.96 (2H), 2.99 (2H, q, J=7.2 Hz), 4.41 (2H, q, J=7.2 Hz), 7.03 (1H), 7.17 (1H, t, J=7.5 Hz), 7.43 (1H, t, J=7.5 Hz), 7.56 (3H), 8.04 (1H, d, J=7.5 Hz), 8.41 (1H), 9.89 (1H, s) ppm Id-3 mp; 287-289° C. $^1$H-NMR (DMSO); 1.20 (3H, t, J=7.2 Hz), 1.28 (2H), 1.47 (6H, d, J=6.9 Hz), 1.50 (2H), 1.85 (8H), 2.23 (1H), 2.26 (2H), 2.72 (2H), 3.00 (2H, q, J=7.2 Hz), 3.04 (1H), 4.57 (1H), 7.03 (1H, d, J=7.5 Hz), 7.10 (1H, d-d, J=8.7, 2.1 Hz), 7.36 (1H, d, J=8.7 Hz), 7.68 (1H, d, J=2.1 Hz), 9.56 (1H, s) ppm Id-4 mp; 120° C. $^1$H-NMR (DMSO); 1.18 (3H, t, J=7.5 Hz), 1.47 (6H, d, J=6.9 Hz), 1.50 (2H), 1.62 (2H), 1.81 (4H), 2.29 (2H, t, J=7.2 Hz), 2.56 (2H), 2.72 (2H), 2.93 (2H), 2.97 (2H, q, J=7.5 Hz), 4.58 (1H), 7.01 (1H), 7.12 (1H, d-d, J=8.7, 2.1 Hz), 7.37 (1H, d, J=8.7 Hz), 7.66 (1H, d, J=2.1 Hz), 9.63 (1H, s) ppm Ie-1 mp; 256-258° C. $^1$H-NMR (DMSO)δ; 1.28 (2H), 1.49 (2H), 1.91 (4H), 2.24 (1H), 3.20 (1H), 4.40 (2H, q, J=9.6 Hz), 4.93 (2H, q, J=9.1 Hz), 6.95 (1H, d, J=8.7 Hz), 7.78 (1H, d, J=7.2 Hz), 7.97 (1H, d-d, J=8.7, 2.7 Hz), 8.39 (1H, d, J=2.7 Hz), 9.96 (1H, s) ppm Ie-2 mp; 234-236° C. $^1$H-NMR (DMSO)δ; 1.27 (2H), 1.48 (2H), 1.91 (4H), 2.46 (1H), 3.20 (1H), 4.40 (2H, q, J=9.9 Hz), 7.79 (1H, s), 8.15 (1H, d-d, J=8.7, 2.1 Hz), 8.27 (1H, d, J=8.7 Hz), 8.69 (1H, d, J=2.1 Hz), 10.87 (1H, s) ppm Ie-3 mp; 143-145° C. $^1$H-NMR (DMSO)δ; 1.56 (4H), 2.32 (2H, t, J=7.2 Hz), 3.01 (2H, t, J=6.6 Hz), 4.37 (2H, q, J=10.2 Hz), 4.93 (2H, q, J=9.3 Hz), 6.95 (1H, d, J=8.7 Hz), 7.74 (1H, s 7.97 (2H, d-d, J=8.7, 2.7 Hz), 8.39 (1H, d, J=2.7 Hz), 10.01 (1H, s) ppm If-1 mp; 239-241° C. $^1$H-NMR (DMSO)6; 1.14 (6H, d, J=6.0 Hz), 1.27 (2H), 1.48 (2H), 1.82 (2H), 1.95 (2H), 2.18 (3H), 3.20 (1H), 3.47 (2H), 3.67 (2H), 4.40 (2H, q, J=9.9 Hz), 6.86 (2H, d, J=9.0 Hz), 7.43 (2H, d, J=9.0 Hz), 7.76 (1H, d, J=7.5 Hz), 9.59 (1H, s) ppm If-2 mp; 128-130° C. $^1$H-NMR (DMSO)δ; 1.14 (6H, d, J=6.3 Hz), 1.55 (4H), 2.21 (4H), 3.00 (2H, t, J=6.6 Hz), 3.48 (2H), 3.68 (2H), 4.37 (2H, q, J=9.9 Hz), 6.86 (2H, d, J=9.3 Hz), 7.42 (2H, d, J=9.3 Hz), 7.34 (1H, s), 9.65 (1H, s) ppm Ig-1 mp; 165-166° C. $^1$H-NMR (DMSO)δ; 1.30 (3H, t, J=7.2 Hz), 2.61 (2H, t, J=7.2 Hz), 3.39 (2H), 4.43 (4H), 7.18 (1H, t, J=7.5 Hz), 7.44 (1H, t, J=7.5 Hz), 7.55 (3H), 7.89 (1H), 8.04 (1H, d, J=7.5 Hz), 8.41 (1H, s), 10.03 (1H) ppm Ih-1 mp; 187-188° C. $^1$H-NMR (DMSO); 1.28 (2H), 1.47 (2H), 1.92 (4H), 2.25 (1H), 2.64 (6H, s 2.98 (1H), 6.48 (1H, d, J=9.9 Hz), 7.13 (1H, d, J=7.8 Hz), 7.35 (1H, d, J=9.0 Hz), 7.64 (1H, d, J=9.3 Hz), 8.05 (1H, d, J=9.0 Hz), 8.07 (1H, s), 10.04 (1H, s) ppm Ih-2 mp; 219-220° C. $^1$H-NMR (DMSO); 1.26 (2H), 1.45 (2H), 1.92 (4H), 2.23 (1H), 2.64 (6H, s 2.98 (1H), 4.93 (2H, q, J=9.0 Hz), 6.95 (1H, d, J=8.7 Hz), 7.13 (1H, s), 7.96 (1H, d-d, J=2.9, 9.0 Hz), 8.40 (1H, d, J=2.4 Hz), 9.94 (1H, s) ppm Ih-3 mp; 164.0-166.0° C. $^1$H-NMR (DMSO); 1.30-1.47 (2H, m), 1.79-1.90 (2H, m), 2.65 (s, 6H), 2.89-3.02 (2H, m), 3.19-3.32 (1H, m), 3.99-4.09 (2H, m), 7.26 (1H, d, J=7.8 Hz), 7.94 (1H, d, J=9.0 Hz), 8.04 (1H, d-d, J=9.0, 1.8 Hz), 8.60 (1H, s), 9.77 (1H, s) ppm Ih-4 mp; 154.0-156.0° C. $^1$H-NMR (DMSO); 1.29-1.45 (2H, m), 1.80-1.90 (2H, m), 2.65 (s, 6H), 2.84-2.98 (2H, m), 3.16-3.32 (1H, m), 3.93-4.04 (2H, m), 4.92 (2H, q, J=9.1 Hz), 6.89 (1H, d, J=9.0 Hz), 7.26 (1H, d, J=8.7 Hz), 7.84 (1H, d-d, J=8.4, 2.4 Hz), 8.21 (1H, d, 2.4 Hz), 8.59 (1H, s) ppm Ii-1 mp; 220-222° C. $^1$H-NMR (DMSO); 1.28 (2H), 1.47 (2H), 1.93 (4H), 2.28 (1H), 2.65 (6H, s 2.99 (1H), 7.14 (1H, d, J=8.1 Hz), 7.65 (2H, d, J=8.1 Hz), 7.80 (2H, d, J=8.1 Hz), 10.18 (1H, s) ppm Ii-2 mp; 220-221° C. $^1$H-NMR (DMSO); 1.25 (2H), 1.44 (2H), 1.88 (4H), 2.18 (1H), 2.64 (6H, s 2.97 (1H), 5.96 (2H, s), 6.82 (1H, d, J=8.1 Hz), 6.95 (1H, d, J=8.1 Hz), 7.13 (1H, d, J=7.8 Hz), 7.30 (1H, s), 9.71 (1H, s) ppm Ii-3 mp; 168-178° C. $^1$H-NMR (DMSO); 1.20-1.50 (m, 4H), 1.82-2.02 (m, 4H), 2.22 (dt, J=12 Hz, 1H), 2.64 (s, 6H), 2.98 (m, 1H), 7.13 (d, J=7.8 Hz, 1H), 7.24 (dd, J=8.7, 2.0 Hz, 1H), 7.33 (d, J=8.4 Hz, 1H), 7.77 (d, J=1.8 Hz, 1H), 10.04 (s, 1H) ppm Ii-4 mp; 218-220° C. $^1$H-NMR (DMSO); 1.20-1.50 (m, 4H), 1.83-2.00 (m, 4H), 2.23 (dt, J=12 Hz, 1H), 2.64 (s, 6H), 3.00 (m, 1H), 7.16 (d, J=8.1 Hz, 1H), 7.35-7.43 (m, 2H), 7.82 (d, J=1.8 Hz, 1H), 10.18 (s, 1H) ppm Ii-5 mp; 230-231° C. $^1$H-NMR (DMSO); 1.30-1.47 (2H, m), 1.80-1.92 (2H, m), 2.66 (s, 6H), 2.87-3.01 (2H, m), 3.18-3.34 (1H, m), 3.95-4.07 (2H, m), 7.26 (1H, d, J=7.8 Hz), 7.57 (2H, d, J=8.7 Hz), 7.67 (2H, d, J=8.7 Hz), 8.90 (1H, s) ppm Ii-6 mp; 155.0-157.0° C. $^1$H-NMR (DMSO); 1.27-1.44 (2H, m), 1.79-1.89 (2H, m), 2.65 (s, 6H), 2.80-2.94 (2H, m), 3.16-3.30 (1H, m), 3.93-4.02 (2H, m), 5.93 (2H, s), 6.77 (1H, d, J=8.4 Hz), 6.82 (1H, d, J=8.7 Hz), 7.12 (1H, s), 7.25 (1H, d, J=7.2 Hz), 8.38 (1H, s) ppm Ij-1 mp; 216-218° C. $^1$H-NMR (DMSO); 1.25 (2H), 1.44 (2H), 1.86 (4H), 2.45 (1H), 2.64 (6H, s 2.98 (1H), 7.14 (1H, d, J=4.5 Hz), 8.15 (1H, d-d, J=2.4, 9.0 Hz), 8.27 (1H, d, J=8.7 Hz), 8.70 (1H, d, J=2.4 Hz), 10.86 (1H, s) ppm Ij-2 mp; 201.0-203.0° C. $^1$H-NMR (DMSO); 1.30-1.46 (2H, m), 1.80-1.93 (2H, m), 2.66 (s, 6H), 2.86-3.00 (2H, m), 3.18-3.36 (1H, m), 3.96-4.08 (2H, m), 6.45 (1H, d, J=9.6 Hz), 7.26 (1H, d, J=8.4 Hz), 7.30 (1H, d, J=9.0 Hz), 7.60 (1H, d, J=8.4 Hz), 7.84 (1H, brs), 8.02 (1H, d, J=9.6 Hz), 8.73 (1H, s) ppm Ij-3 mp; 219-221° C. $^1$H-NMR (DMSO); 1.22-1.52 (m, 4H), 1.73-2.00 (m, 10H), 2.24 (dt, J=12 Hz, 1H), 2.60 (m, 2H), 2.64 (s, 6H), 2.88 (m, 2H), 2.99 (m, 1H), 7.16 (d, J=7.8 Hz, 1H), 7.24 (dd, J=8.7, 2.0 Hz, 1H), 7.33 (d, J=8.7 Hz, 1H), 7.83 (s, 1H), 9.79 (s, 1H) ppm Experiment 1

Antifeeding Activity

A guide cannula was implanted in ventriculus lateralis of 7-week-old rats (200-300 g) reared in free-feeding. Then the rats reared in free-feeding about for 1 week.

A compound of the present invention was suspended in 0.5% HPMC solution (hydroxypropylmethylcellulose: 60SH-50, Shin-Etsu Chemical Co., Ltd.) to get a final concentration of 15 mg/ml.

Rats were given 2 mL/kg of a suspension of a compound of the present invention (the compound 30 mg/kg) by oral administration. On the other hand, rats in a control group were given the same amount of 0.5% HPMC by oral administration.

NPYY5 agonist ([cPP$^{1-7}$, NPY$^{19-23}$, Ala$^{31}$, Aib$^{32}$, Gln$^{34}$]-hPancreatic Polypeptide: Tocris Coockson) was dissolved in a physiological salt solution to be 0.1 nmol/10 μL. 0.1 nmol of the solution was infused via a guide cannula in a head of the rat one hour after giving a compound of the present invention. Immediately after the infusion, the amount of the remaining food was measured.

The amount of the remaining food was measured 1, 2 or 4 hour(s) after the infusion of an agonist and the food intake for this period was calculated. An antifeeding rate of a compound of the present invention against the food intake of rats in a control group was calculated. The results were shown below.

TABLE 1

| Compound | Antifeeding activity (%) | | |
|---|---|---|---|
| No. | 1 h | 2 h | 4 h |
| Ia-2 | 98** | 77** | 56** |
| Ia-3 | 85** | 78** | 74** |
| Ib-1 | 90** | 95** | 92** |
| Id-1 | 5 | 37 | 49** |
| Id-2 | 100** | 100** | 100** |
| Id-4 | 100** | 94** | 95** |
| Ie-3 | 56 | 62* | 21 |
| Ig-1 | 67 | 44 | 48** |
| Ii-1 | 42 | 38* | 31 |

*p < 0.05,
**p < 0.01

The above results showed that a compound of the present invention significantly inhibited the food intake of rats.

Formulation Example 1

Tablets

| | |
|---|---|
| Compound (Ia-1) | 15 mg |
| Starch | 15 mg |
| Lactose | 15 mg |
| Crystalline cellulose | 19 mg |
| Polyvinyl alcohol | 3 mg |
| Distilled water | 30 ml |
| Calcium stearate | 3 mg |

After all of the above ingredients except for calcium stearate are uniformly mixed, the mixture is crushed and granulated, and dried to obtain a suitable size of granules. After calcium stearate is added to the granules, tablets are formed by compression molding.

Formulation Example 2

Capsules

| | |
|---|---|
| Compound (Ib-1) | 10 mg |
| Magnesium stearate | 10 mg |
| Lactose | 80 mg |

After the above ingredients are mixed to prepare powders or granules, the obtained are filled in capsules.

Formulation Example 3

Granules

| Compound (Ic-1) | 30 g |
|---|---|
| Lactose | 265 g |
| Magnesium Stearate | 5 g |

After the above ingredients are mixed uniformly and formed by compression molding, the obtained are crushed, granulated and sieved to prepare suitable volume of granules.

INDUSTRIAL APPLICABILITY

As shown in the above Experiments, the compounds of the present invention have an NPY Y5 receptor antagonistic activity. Therefore, the compounds of the present invention are very useful as an anti-obestic agent and anorectic agent.

The invention claimed is:

1. A compound of the formula (I):

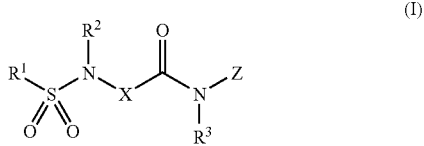

wherein, $R^1$ is amino optionally substituted by lower alkyl, $R^2$ and $R^3$ are each independently hydrogen or lower alkyl, X is piperidinediyl, Z is optionally substituted phenyl or optionally substituted hetercyclyl, or a pharmaceutically acceptable salt thereof.

2. The compound, or pharmaceutically acceptable salt thereof described in claim 1 wherein X is

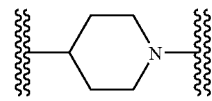

3. The compound or, pharmaceutically acceptable salt thereof described in claim 1 wherein Z is
   (i) phenyl optionally substituted by one or more substituent(s) selected from morpholino substituted by lower alkyl, halogeno lower alkyl, lower alkoxy, lower alkoxycarbonyl, lower alkylene dioxy or halogene lower alkylene dioxy,
   (ii) pyridyl optionally substituted by one or more substituent(s) selected from halogeno lower alkyl or halogeno lower alkoxy,
   (iii) carbazolyl optionally substituted by lower alkyl or tetrahydrocarbazolyl optionally substituted by lower alkyl,
   (iv) benzofuryl optionally substituted by one or more substituent(s) selected from lower alkoxy, lower alkoxycarbonyl or lower alkyl carbamoyl,
   (v) chromenyl optionally substituted by oxo or
   (vi) cycloheptabenzofuryl.

4. The compound or pharmaceutically acceptable salt thereof described in claim 1 wherein both $R^2$ and $R^3$ are hydrogen.

5. A pharmaceutical composition comprising the compound or pharmaceutically acceptable salt thereof described in claim 1.

* * * * *